United States Patent
Jeppsson et al.

(10) Patent No.: US 6,327,895 B1
(45) Date of Patent: Dec. 11, 2001

(54) METHOD AND ARRANGEMENT FOR INTEGRITY-TESTING OF A TUBE-SET FOR USE IN A CYCLER FOR PERITONEAL DIALYSIS

(75) Inventors: Jan-Bertil Jeppsson, Lomma; Bengt-Olov Thell, Flyinge, both of (SE)

(73) Assignee: Gambro Lundia AB (CH)

( * ) Notice: Subject to any disclaimer, the term of this patent is extended or adjusted under 35 U.S.C. 154(b) by 0 days.

(21) Appl. No.: 09/446,486

(22) PCT Filed: Jul. 6, 1998

(86) PCT No.: PCT/SE98/01325

§ 371 Date: Dec. 21, 1999

§ 102(e) Date: Dec. 21, 1999

(87) PCT Pub. No.: WO99/02206

PCT Pub. Date: Jan. 21, 1999

(30) Foreign Application Priority Data

Jul. 9, 1997 (SE) .................................................. 9702646

(51) Int. Cl.$^7$ .................................................. G01M 3/04
(52) U.S. Cl. .............................. 73/40; 73/40.5 R; 73/37; 604/29
(58) Field of Search ................... 73/37, 40, 40.5 R, 73/46, 49.1, 49.5; 604/29

(56) References Cited

U.S. PATENT DOCUMENTS

| | | | |
|---|---|---|---|
| 5,350,357 | * 9/1994 | Kamen et al. | ............................ 604/29 |
| 5,411,682 | * 5/1995 | Nagashima | .............................. 264/36 |
| 5,624,551 | * 4/1997 | Baumann et al. | ..................... 210/134 |
| 5,674,404 | * 10/1997 | Kenley et al. | ......................... 210/741 |
| 5,711,883 | * 1/1998 | Folden et al. | .......................... 210/646 |
| 6,044,691 | * 4/2000 | Kenley et al. | ...................... 73/40.5 R |
| 6,187,207 | * 2/2001 | Brauer | .................................. 210/739 |

FOREIGN PATENT DOCUMENTS

| | | | |
|---|---|---|---|
| WO 95/20985 | 8/1995 | (WO) | .............................. A61M/1/28 |
| 96/40322 | 12/1996 | (WO) | .............................. A61M/1/36 |
| WO 97/11770 | 4/1997 | (WO) | .............................. B01D/61/32 |

* cited by examiner

*Primary Examiner*—Daniel S. Larkin
*Assistant Examiner*—Charles D. Garber
(74) *Attorney, Agent, or Firm*—Lerner, David, Littenberg, Krumholz & Mentlik, LLP (57) ABSTRACT

Methods and apparatus are disclosed for testing the integrity of a tube set used in a cycler for peritoneal dialysis comprising a closable housing for at least a portion of the tube set and an air pump for subjecting the housing to an underpressure or an overpressure, and clamps for clamping portions of the tube set passing into the housing. The method includes subjecting the housing to a first overpressure with the clamps closed whereby a first pressure leakage is observed, subjecting the housing to a second overpressure with the clamps open whereby a second pressure leakage is observed, and comparing the first and second pressure leakages so that action can be taken based upon that comparison.

10 Claims, 3 Drawing Sheets

METHOD AND ARRANGEMENT FOR INTEGRITY-TESTING OF A TUBE-SET FOR USE IN A CYCLER FOR PERITONEAL DIALYSIS

TECHNICAL FIELD

The present invention relates to a method and an arrangement in a machine for carrying out peritoneal dialysis. More specifically, the invention relates to a method and arrangement for integrity-testing of a tube-set for use in a cycler for peritoneal dialysis

PRIOR ART

Peritoneal dialysis, hereinafter abbreviated to PD, can be carried out more or less manually in a so-called CAPD treatment, where CAPD stands for "continues ambulatory peritoneal dialysis" or with help of a machine in a so-called APD treatment, where APD stands for "automated peritoneal dialysis".

Liquid for PD is delivered in a sterile form in supply bags which are connected to the patient via a tubeset and a catheter which terminates in the abdominal cavity of the patient. When used in connection with APD, the tube-set comprises a heat bag to which the PD liquid is initially conveyed in order to be heated to body temperature. The liquid has a composition which is suitable for PD. Normally, it includes glucose as an osmotic agent.

A machine which is commonly termed a cycler is used during APD for regulating the supply and removal of liquid to and from the peritoneal cavity in the patient's abdominal cavity via the catheter.

Such a cycler is described in WO 95/20985 and comprises a casing which encases said heat bag as well as a discharge bag. An underpressure and an overpressure respectively can be created in the casing via an air pump to thereby drive the liquid into and out of the bags. Inlets and outlets to the bags pass through respective bushings in the wall of the casing.

A problem which arises in connection with a cycler of the type which is described in WO 95/20985 is the following. If there is a hole in that portion of the tube-set which is located within the casing, i.e. a leak in the bag, the connection between tube and bag or the tube from the bag to or in the bushing, there is a risk that PD liquid can leak out of the bag and collect at the base of the casing.

Such a hole may arise due to faulty material, because the welding between the bag and the tube is unsatisfactory or due to the effect of a sharp object in connection with the use or other careless handling of the bag.

U.S. Pat. No. 5,350,357 discloses a cycler comprising leak testing of the disposable set. Such leak testing is performed as a one step procedure at low or high pressure. This leak testing procedure requires access to the interior of the disposable set.

SUMMARY OF THE INVENTION

It is therefore the object of the present invention to provide a method and an arrangement which permits checking if there is a risk of leakage.

In accordance with the invention, the portion of the tube-set which is located within the casing is subjected to an integrity-test before the machine is allowed to commence the dialysis treatment.

The machine is started and performs its normal function test in which all of the essential functions and safety systems of the machine are tested. During this function test, the machine is attired with the sterile tube-set. Supply bags are connected to the inlet tubes. The patient connection is placed in a special priming position. When the function test has been performed, the machine adopts a stand-by condition. When the patient has attached the tube-set, the patient presses a pre-rinse button. Before the actual pre-rinse or priming of the tube-set, an integrity-test according to the invention is performed.

By means of an air pump, an overpressure of a predetermined amount is created in the casing outside the tube-set, whereby the outlets from the tube-set are open. When the predetermined air pressure has been reached, the pump is stopped and the clamp arrangements are closed. The air can thus exit the casing via a possible leakage which is always present in such a construction, for example between the cover and base of the casing or via the bushings. A "normal" leakage implies that the pressure slowly reduces. The pressure sequence is recorded using a pressure meter for a predetermined interval of time.

Thereafter, the pressure is once more increased in the casing to said predetermined pressure and the outlets via the tube-set are opened by means of clamps. The pressure sequence is once more recorded using the pressure meter for a predetermined interval of time.

If the pressure sequences are substantially identical for the first two tests, it is an indication that the tube-set has passed the integrity-test. The tube-set is thereafter filled with liquid in a so-called priming stage.

If, on the other hand, the second pressure sequence leads to a more rapid reduction of the pressure than the first pressure sequence, it is an indication that there is a fault present. Thus, the machine can emit an alarm signal. Furthermore, the machine can be placed in a condition which renders impossible continued use until a new tube-set is mounted and a new integrity-test has been executed.

Alternatively, the integrity-test can be performed with underpressure in the casing or underpressure and overpressure in combination. Other alternatives will be apparent from the following description.

According to the invention, the difference in final pressure is not allowed to be greater than the predetermined pressure differential value for the machine to be able to recognise that the integrity-test has been executed in a satisfactory manner. Other methods of calculation can also be used.

The integrity-test can be combined with devices for sensing whether liquid has leaked onto the base of the casing.

Thus, it is apparent that the invention makes possible a leak test without intervening into the interior of the tube-set, which is sterilised before use and should be kept sterile. The invention discriminates between a "normal" leakage and a leakage through a hole, which cannot be tolerated.

The invention will be described in greater detail below with reference to an embodiment of the invention shown in the drawings.

DETAILED DESCRIPTION OF THE INVENTION

Figure 1:
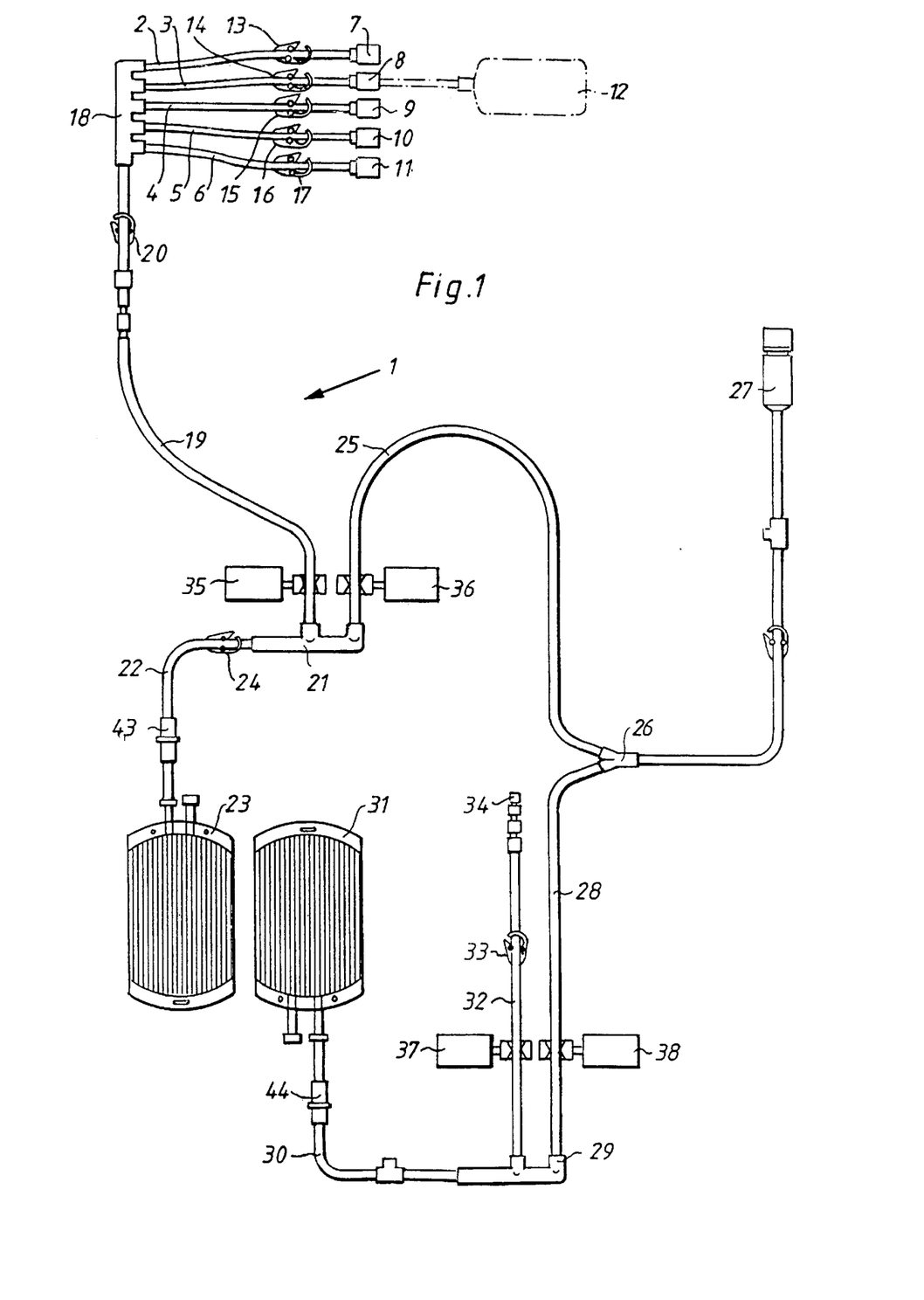
FIG. 1 is a side-view of a tube-set intended for peritoneal dialysis and on which the present invention can be applied.
Figure 2:
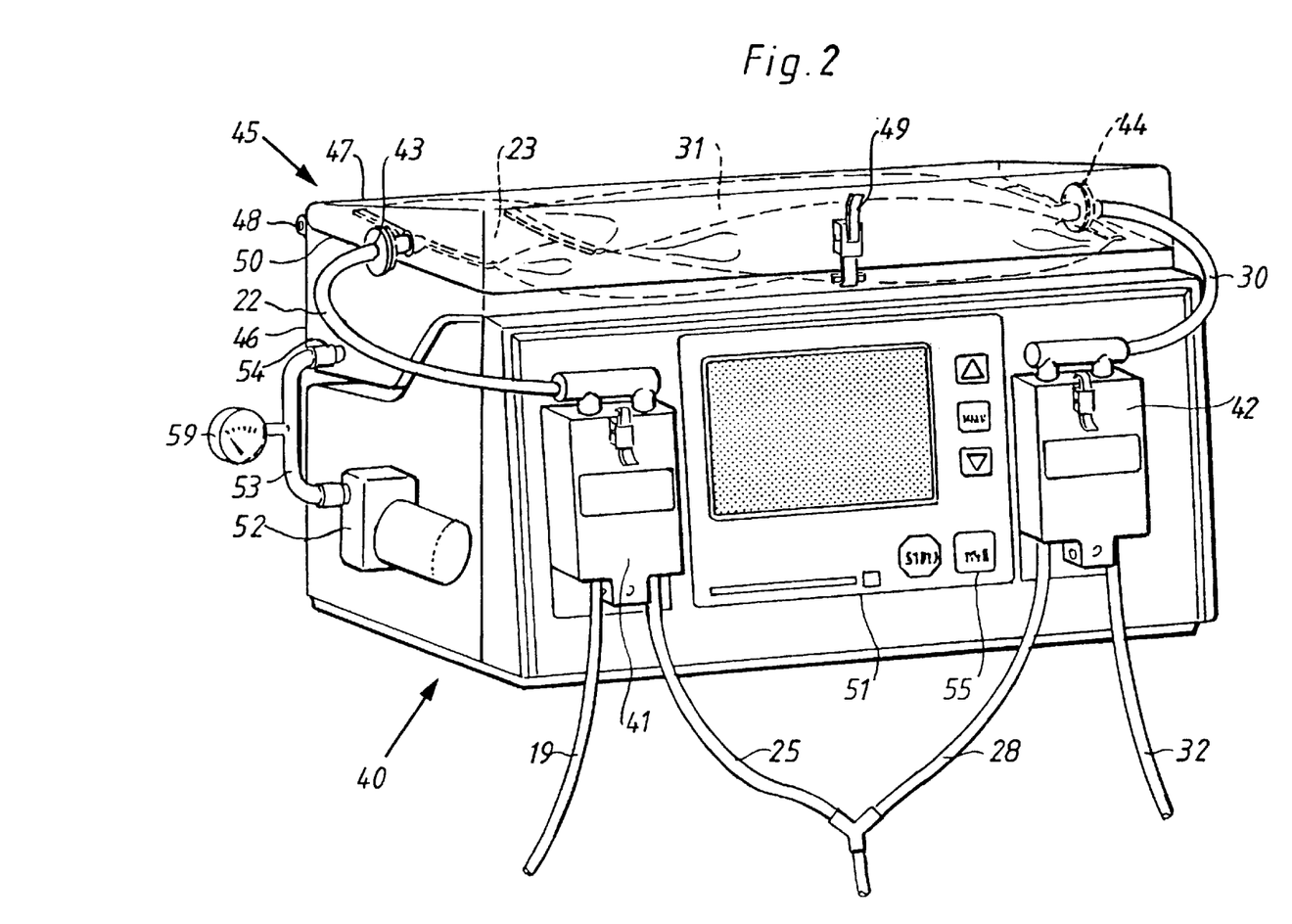
FIG. 2 is a perspective view of a cycler of a known type and equipped with the tube-set according to FIG. 1 and on which the present invention is intended to be applied.

The invention is intended to be used together with a cycler which is shown in FIG. 2 and a tube-set which is shown in FIG. 1, which drawings are taken from WO 95/20985.

The tube-set 1 is provided with a plurality of inlet tubes 2, 3, 4, 5, 6 provided with connectors 7, 8, 9, 10, 11 for connection to supply bags 12 of dialysis-solution, whereof only one is shown with dashed lines in FIG. 1. The number of tubes 2-6 is of course dependent on the application and is normally either five or ten. Each tube is provided with a tube clamp 13, 14, 15, 16, 17 which, in the shown embodiment, is manually operable.

The tubes 2–6 lead to a manifold coupling 18 and the flows combine into a common first tube 19 which leads to an F-coupling 21. The tube 19 has a tube clamp 20. A second tube 22 runs from the F-coupling to a heat bag 23. The tube 22 is provided with a tube clamp 24. A third tube 25 runs from the F-coupling via a Y-coupling 26 to a connection 27 intended to be connected to a catheter of the patient. A fourth tube 28 runs from the Y-coupling 26 to a second F-coupling 29. A fifth tube 30 runs from the F-coupling 29 to a discharge bag 31. In addition, a sixth tube 32 provided with a tube clamp 33 runs from the F-coupling 29 to a connector 34. The connector 34 is intended to be connected to a drain or a large container (which can be a number of used supply bags).

The first tube 19, the third tube 25, the fourth tube 28 and the sixth tube 32 are provided with electromagnetically controlled clamp arrangements 35, 36, 37 and 38 which are actuated electrically. The heat bag 23 and the discharge bag 31 are located in a pressure chamber as is more clearly apparent from FIG. 2.

The tube-set 1 shown in FIG. 1 is intended to be used in a cycler 40 which is shown in FIG. 2. The tube-set is only partially shown in FIG. 2. The electromagnetically controlled clamp arrangements are arranged pair-wise in clamp holders so that the clamp arrangements 35 and 36 are located in a first clamp holder 41 and the clamp arrangements 37 and 38 are located in a second clamp holder 42.

It is apparent from FIG. 2 that the tube 22 is provided with a bushing 43 and the tube 30 is provided with a bushing 44. The heat bag 23 and the discharge bag 31 are located in a casing 45 which consists of a lower portion or a base 46 and an upper portion or a cover 47, which cover is affixed to the base via a hinge 48. A locking device 49 holds the cover 47 and the base 46 together so that the seal 50 there between is compressed and a substantially airtight joint is attained between the cover and the base. The bushings 43 and 44 fit into recesses in the cover and/or the base.

The cycler 40 comprises a display and control unit 51 positioned on the front of the machine. Furthermore, there is an air pump 52 which, via a tube 53, communicates with a connection 54 on the side of the casing. The connection 54 leads to the interior of the casing.

Figure 3:
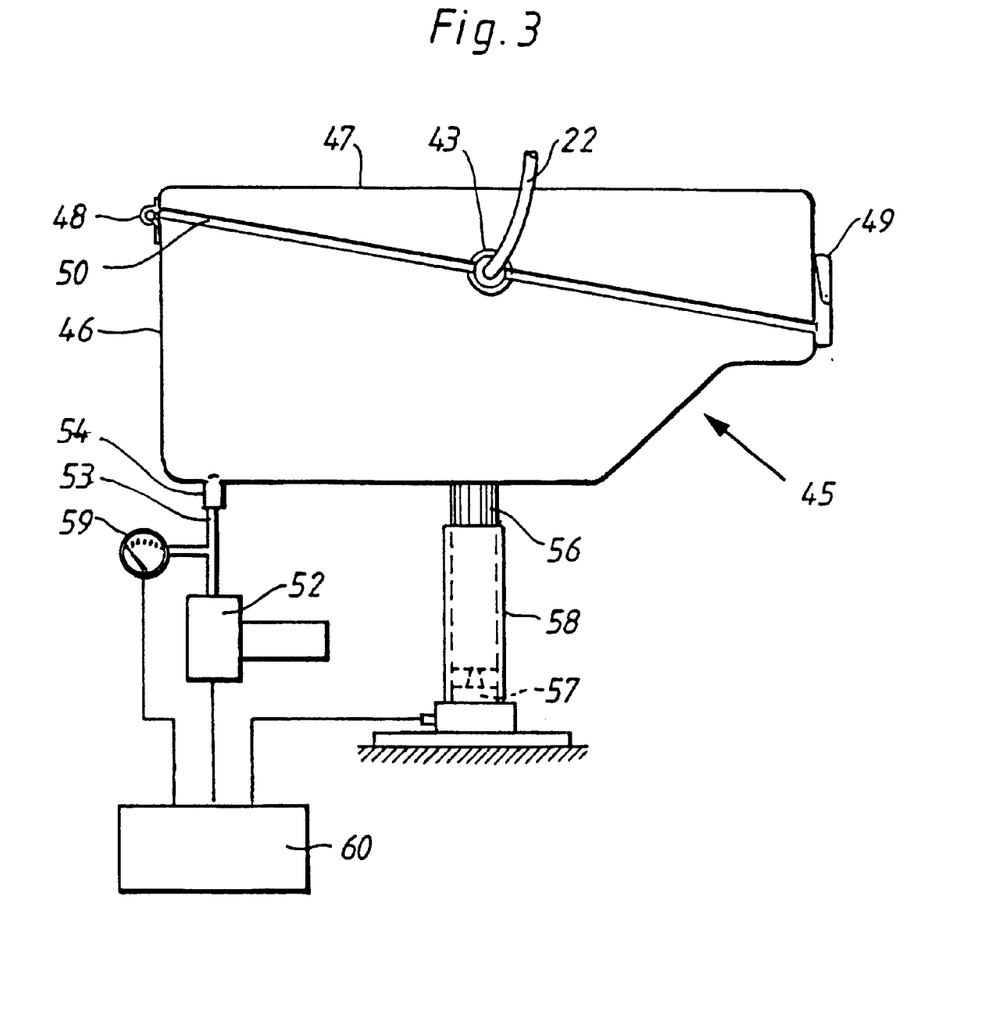
FIG. 3 is a side-view of a portion of the cycler according to FIG. 2 provided with the arrangement according to the invention.

As is shown in FIG. 3, the base of the casing is provided at its centre with a vertical rod 56 which rests on a load cell 57. The rod is inserted into a sleeve 58 arranged on the load cell such that the casing cannot lean in any direction. The casing 45 with contents can thus be weighed by the load cell 57.

The normal operation of this cycler is described in Wo 95/20985. Briefly, the air pump 52 is used to create underpressure and overpressure in the casing 45.

A cycle commences with the heat bag containing PD liquid which has been heated to body temperature.

The catheter of the patient is connected to the connector 27 and a drainage phase commences by opening the clamp arrangement 37 at the same time that an underpressure prevails in the casing 45 where the drainage bag 31 is located. The bag 31 is thus filled with used PD solution from the patient which is monitored by the load cell.

When the drainage phase has taken place, the clamp arrangement 37 is closed and the clamp arrangement 36 is opened and connects the heat bag to the patient. At the same time, the pump 52 is operated so that an overpressure prevails in the casing 45. The contents of the heat bag are now transferred to the patient during monitoring of the load cell.

When a suitable quantity has been transferred, the clamp arrangement 36 is closed and the clamp arrangement 38 is opened. The pump 52 still creates an overpressure in the casing 45 so that, during monitoring via the load cell, the drainage bag is emptied into a vessel connected to the connector 34 (or directly to the drain).

Finally, the clamp arrangement 38 is closed and the clamp arrangement 35 is opened at the same time that an underpressure is created by the pump in the casing. New PD solution is supplied to the heat bag 23 from supply bags 12 connected to the connectors 7–11 during monitoring of the load cell. The new PD solution is heated to body temperature and the cycler is ready for a new cycle.

Reference is made to WO 95/20985 for a more detailed description of the sequence. WO 95/20985 is incorporated herein by reference.

If the tube-set has a leak in that portion which is within the casing, problems arise. If the leakage is great, which can be the case when there is faulty welding, the entire casing can be more or less filled with PD solution. There is a risk that the solution in the casing will thereafter be fed to the patient. In other cases, there is a risk that air will be fed to the patient instead of PD solution. It is obvious that such conditions must be avoided.

If there are small holes, there is always the risk that bacteria can enter through the holes and cause infection. Such contamination should also be avoided, for which reason it is just as important to be able to detect small holes.

It is possible to provide the cycler with mechanical or electrical sensors which sense if liquid is present in the lower portion of the base 46. However, such liquid sensors require maintenance and can themselves result in faulty operation.

By arranging the connection 54 of the pump in the lowest portion of the casing, any liquid in the casing will be drawn to the pump during the underpressure portion of the cycler's function. Such liquid in the pump can be electronically sensed and used to actuate an alarm signal.

These mechanical arrangements are, however, not able to take care of the situation in which air is fed into the conduit to the patient. Possibly, this can be detected by the load cell registering a too small quantity of liquid fed to the patient.

In accordance with the present invention, another method is however provided to remove the above-mentioned problem. The tube-set is subjected to an integrity-test before it is filled with liquid for the first time.

The tube-set is mounted to the cycler as has been described above and a desired number of supply bags 12 are connected to the connections 7–11 and corresponding clamps 13–17 are opened. It is further ensured that the tube clamps 20, 24, 33 are open and that the clamp arrangements 35–38 are closed. Thereafter, the button 55 is pressed for pre-rinsing or priming. Initially, however, an integrity-test is performed according to the invention. If the integrity-test is carried out faultlessly, the machine continues with priming and pre-rinsing of the tube-set as normal. Since the integrity-test takes only a short time, the patient will not normally notice that an integrity-test is taking place.

During the integrity-test, the pump 52 is activated at the same time that the clamp arrangements 36 and 37 are opened and an overpressure is attained in the casing 45. The overpressure can for example be 40 mm Hg. Finally, the clamp arrangements 36 and 37 are closed and the pump is stopped, whereupon the pressure in the casing will slowly start to drop due to the fact that the air exits through the seal between the cover and base as well as via the bushings. This first "normal" pressure sequence is monitored by a pressure meter 59 connected to the interior of the casing 45. After a predetermined interval of time, for example 10 seconds, the final pressure is read and the pressure drop is read as $\Delta P_1$.

The pump is reactivated to increase the pressure to the same pressure as before, i.e. for example 40 mm Hg. When the pump stops, the clamp arrangements 36 and 37 are opened and the pressure slowly drops again in the same manner as during the first pressure sequence. If a hole is present in the portion of the tube-set which is located in the casing, air will also pass through this hole to either the heat bag or the discharge bag and thereafter out to the atmosphere via the open tube 19 or the tube 32. After the predetermined interval of time, the pressure reduction is read as $\Delta P_2$.

If this second pressure sequence is the same as the first pressure sequence, it is an indication that the tube-set does not have a leak. If the pressure in the second pressure sequence drops more quickly than during the first pressure sequence, it is an indication that there is a leak since, during the second pressure sequence, a quicker pressure drop occurs because of leakage which is released via the open connection 27.

If the difference between $\Delta P_2$ and $\Delta P_1$ is less than a predetermined value $\Delta P$, for example less than 2 mm Hg, it is regarded that the tube-set has passed the integrity-test. $\Delta P$ is selected such that normal variations in the pressure drop do not activate the integrity-test. In addition, other stipulations can be made separately or in combination, for example that $\Delta P_2$ may not be more than 50% greater than $\Delta P_1$. The calculations are performed in a control unit 60 in the form of a microprocessor.

Our experiments show that, using this method, we are able to detect holes having a diameter less than about 0.3–0.4 mm.

If the hole is located at the far end of the bag, it may occur that the bag collapses and prevents air from passing via the hole and to the tubes and eventually out. This could imply that a tube-set which has a hole could pass the integrity-test. To avoid this, the bags are ribbed internally in the longitudinal direction so that there is always a flow-path for the air.

Naturally, an integrity-test according to the present invention cannot replace the check which the user should always make to the cycler at suitable occasions. If liquid is present at the bottom of the casing, the reason for this should always be investigated.

A combination of underpressure and overpressure can also possibly be used.

Instead of waiting for a predetermined interval of time, 10 seconds, the pressure can be allowed to drop to a predetermined pressure, for example 30 mm Hg, and the time can be measured that it takes to attain the second lower pressure.

The order of the two pressure sequences can be reversed so that a possibly greater leakage is detected first by opening the clamp arrangements 36 and 37 and thereafter a normal leakage is established.

It is also possible to firstly attain the higher pressure of 40 mm Hg and thereafter allow the pressure to drop with the clamp arrangements closed for a certain time, for example 10 seconds, and read the pressure and is thereafter directly open the clamp arrangements and permit the pressure to continue to drop without firstly increasing the pressure and finally recording the pressure after a further time interval, for example 9 seconds. The ratio between the pressure differences provides an indication of whether the pressure reduction is quicker when the clamp arrangements are open.

The pressure during the two phases does not need to be the same. Instead, different pressures can be used and the comparison can take place on the basis of calculations which are determined theoretically and/or empirically.

It is also possible to keep the pressure constant, for example at 40 mm Hg, by driving the pump and measuring the quantity of air which is fed into the chamber which thus will be the same as the leakage.

The above-described methods can be used individually or in suitable combinations.

The invention has been described above with reference to preferred embodiments of the invention. A skilled person will realise that further possibilities for use of the invention exist which are within the scope of the invention and such possibilities and modifications are within the scope of the invention. The invention is restricted only by the appended claims.

What is claimed is:

1. A method for testing the integrity of a tube set used in a cycler for peritoneal dialysis comprising a closable housing for at least a portion of said tube set and pressure means for subjecting said housing to an underpressure or an overpressure, and including clamps for clamping portions of said tube set passing into said housing, said tube set containing air and said method comprising
    subjecting said housing to a first overpressure with said clamps closed, whereby a first pressure leakage can be observed,
    subjecting said housing to a second overpressure with said clamps open, whereby a second pressure leakage can be observed, and
    comparing said first and second pressure leakages, whereby action can be taken based upon said comparison.

2. The method of claim 1 wherein said first and second overpressures are substantially the same, and wherein said comparing of said first and second pressure leakages determines whether said difference or ratio between said first and second pressure leakages exceeds a predetermined value, whereby action can be taken if said predetermined value is exceeded.

3. The method of claim 1 wherein said observing of said first and second pressure leakages comprises monitoring said pressure leakage with a pressure sensor, whereby said pressure leakage comprises a pressure drop over a predetermined time period or until a predetermined pressure drop is obtained within a predetermined time period.

4. The method of claim 1 wherein said subjecting of said housing to said first and second overpressure comprises connecting an air pump to the lower portion of said housing, and including monitoring the entry of liquid into said air pump.

5. The method of claim 1 including monitoring the presence of liquid in the lower portion of said housing by means of a liquid sensor disposed in said housing.

6. Apparatus for testing the integrity of a tube set used in a cycler for peritoneal dialysis comprising a closable housing for at least a portion of said tube set, said apparatus comprising:

pressure means for subjecting said housing to an overpressure or an underpressure, clamps for clamping portions of said tube set passing into said housing, whereby when said housing is subjected to a first overpressure with said clamps closed a first pressure leakage can be observed and when said housing is subjected to a second overpressure with said clamps open a second pressure leakage can be observed, and control means for comparing said first and second pressure leakages, whereby action can be taken based on said comparison.

7. The apparatus of claim 6 wherein said first and second overpressures are substantially the same, and wherein said control means compares said first and second pressure leakages to determine if the difference or ratio between said first and second pressure leakages exceeds a predetermined value, whereby action can be taken if said predetermined value is exceeded.

8. The apparatus of claim 6 wherein said pressure means comprises a pressure sensor for monitoring said pressure leakage, whereby said pressure leakage comprises a pressure drop over a predetermined time period or until a predetermined pressure drop is obtained within a predetermined time period.

9. The apparatus of claim 6 wherein said pressures means comprises an air pump connected to the lower portion of said housing, whereby the entry of liquid into said air pump can be monitored.

10. The apparatus of claim 6 including a liquid sensor disposed in said housing for monitoring the presence of liquid in a lower portion of said housing.

* * * * *

UNITED STATES PATENT AND TRADEMARK OFFICE
CERTIFICATE OF CORRECTION

PATENT NO.    : 6,327,895 B1
DATED         : December 11, 2001
INVENTOR(S)   : Jan-Bertil Jeppsson and Bengt-Olov Thell It is certified that error appears in the above-identified patent and that said Letters Patent is hereby corrected as shown below:

<u>Title page,</u>
Item [73], Assignee, delete "(CH)" and insert therefor -- (SE) --.

<u>Column 8,</u>
Line 11, "pressures" should read -- pressure --.

Signed and Sealed this

Twenty-fifth Day of October, 2005

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 6,327,895 B1 | Page 1 of 5 |
| APPLICATION NO. | : 09/446486 | |
| DATED | : December 11, 2001 | |
| INVENTOR(S) | : Jeppsson et al. | |

It is certified that error appears in the above-identified patent and that said Letters Patent is hereby corrected as shown below:

IN THE SPECIFICATION PLEASE DELETE COLUMNS 1 THROUGH 8 LINES 1 THROUGH 24 AND INSERT THE ATTACHED SPECIFICATION COLUMNS 1 THROUGH 8 AS FOLLOWS.

Signed and Sealed this

Thirty-first Day of July, 2007

JON W. DUDAS
*Director of the United States Patent and Trademark Office*

METHOD AND ARRANGEMENT FOR INTEGRITY-TESTING OF A TUBE-SET FOR USE IN A CYCLER FOR PERITONEAL DIALYSIS

FIELD OF THE INVENTION

The present invention relates to a method and apparatus for use with a machine for carrying out peritoneal dialysis. More specifically, the present invention relates to a method and apparatus for integrity-testing of a tube-set for use in a cycler for peritoneal dialysis.

BACKGROUND OF THE INVENTION

Peritoneal dialysis, hereinafter referred to as PD, can be carried out more or less manually in a so-called CAPD treatment, where CAPD stands for "continuos ambulatory peritoneal dialysis" or with the assistance of a machine in a so-called APD treatment, where APD stands for "automated peritoneal dialysis".

Liquid for PD is delivered in a sterile form in supply bags which are connected to the patient through a tube-set and a catheter which terminates in the abdominal cavity of the patient. When used in connection with APD, the tube-set comprises a heat bag to which the PD liquid is initially conveyed in order to be heated to body temperature. The liquid has a composition which is suitable for PD. Normally, it includes glucose as an osmotic agent.

A machine which is commonly termed a cycler is used during APD for regulating the supply and removal of liquid to and from the peritoneal cavity in the patient's abdominal cavity through the catheter.

Such a cycler is described in PCT Application No. WO 95/20985 and comprises a casing which encases the heat bag as well as a discharge bag. An underpressure and an overpressure can be created in the casing by means of an air pump to drive the liquid into and out of the bags. Inlets and outlets to the bags pass through respective bushings in the wall of the casing.

A problem which arises in connection with a cycler of the type which is described in PCT Application No. WO 95/20985 is the following. If there is a hole in that portion of the tube-set which is located within the casing, i.e. a leak in the bag, the connection between tube and bag or the tube from the bag to or in the bushing, there is a risk that PD liquid can leak out of the bag and collect at the base of the casing.

Such a hole may arise due to faulty material, because the welding between the bag and the tube is unsatisfactory, or due to the effect of a sharp object in connection with the use or other careless handling of the bag.

U.S. Pat. No. 5,350,357 discloses a cycler comprising leak testing of the disposable tube set. Such leak testing is performed as a one step procedure at low or high pressure. This leak testing procedure requires access to the interior of the disposable set.

It is therefore the object of the present invention to provide a method and apparatus which permits checking if there is a risk of leakage.

SUMMARY OF THE INVENTION

In accordance with the present invention, this and other objects have now been realized by the discovery of a method for testing the integrity of a tube set used in a cycler for peritoneal dialysis comprising a closable housing for at least a portion of the tube set and pressure means for subjecting the housing to an underpressure or an overpressure, and including clamps for clamping portions of the tube set passing into the housing, the tube set containing air, and the method comprising subjecting the housing to a first overpressure with the clamps closed, whereby a first pressure leakage can be observed, subjecting the housing to a second overpressure with the clamps open, whereby a second pressure leakage can be observed, and comparing the first and second pressure leakages, whereby action can be taken based upon the comparison. In a preferred embodiment, the first and second overpressures are substantially the same, and the comparing of the first and second pressure leakages determines whether the difference or ratio between the first and second pressure leakages exceeds a predetermined value, whereby action can be taken if the predetermined value is exceeded.

In accordance with one embodiment of the method of the present invention, observing of the first and second pressure leakages comprises monitoring the pressure leakage with a pressure sensor, whereby the pressure leakage comprises a pressure drop over a predetermined time period or until a predetermined pressure drop is obtained within a predetermined time period.

In accordance with another embodiment of the method of the present invention, subjecting of the housing to the first and second overpressure comprises connecting an air pump to the lower portion of the housing, and includes monitoring the entry of liquid into the air pump.

In accordance with another embodiment of the method of the present invention, the method includes monitoring the presence of liquid in the lower portion of the housing by means of a liquid sensor disposed in the housing.

In accordance with the present invention, apparatus has also been discovered for testing the integrity of a tube set used in a cycler for peritoneal dialysis comprising a closable housing for at least a portion of the tube set, the apparatus comprising pressure means for subjecting the housing to an overpressure or an underpressure, clamps for clamping portions of the tube set passing into the housing, whereby when the housing is subjected to a first overpressure with the clamps closed a first pressure leakage can be observed and when the housing is subjected to a second overpressure with the clamps open a second pressure leakage can be observed, and control means for comparing the first and second pressure leakages, whereby action can be taken based on the comparison. In a preferred embodiment, the first and second overpressures are substantially the same, and the control means compares the first and second pressure leakages to determine if the difference or ratio between the first and second pressure leakages exceeds a predetermined value, whereby action can be taken if the predetermined value is exceeded.

In accordance with one embodiment of the apparatus of the present invention, the pressure means comprises a pressure sensor for monitoring the pressure leakage, whereby the pressure leakage comprises a pressure drop over a predetermined time period or until a predetermined pressure drop is obtained within a predetermined time period.

In accordance with another embodiment of the apparatus of the present invention, the pressure means comprises an air pump connected to the lower portion of the housing, whereby the entry of liquid into the air pump can be monitored.

In accordance with another embodiment of the apparatus of the present invention, the apparatus includes a liquid

```
ERROR: interrupt
OFFENDING COMMAND: xfile

STACK:

false
[0 ]
1
false
false
1303
887
1
1
1
8
1
1
```